United States Patent [19]
Chang et al.

[11] Patent Number: 5,821,270
[45] Date of Patent: Oct. 13, 1998

[54] SLURRY HYDROCARBON SYNTHESIS PROCESS WITH MULTISTAGE CATALYST REJUVENATION

[75] Inventors: Min Chang, Warren; Constantine A. Coulaloglou, Mendham, both of N.J.; Stephen Ju-Ming Hsia, Baton Rouge, La.; Charles John Mart, Coppell, Tex.

[73] Assignee: Exxon Research and Engineering Company, Florham Park, N.J.

[21] Appl. No.: 850,356

[22] Filed: May 2, 1997

[51] Int. Cl.⁶ .................................................. C07C 27/00
[52] U.S. Cl. ......................... 518/700; 518/715; 502/21; 502/22; 502/53
[58] Field of Search ..................... 518/700, 715; 502/21, 22, 53

[56] References Cited

U.S. PATENT DOCUMENTS

| | | |
|---|---|---|
| 5,260,239 | 11/1993 | Hsia .............................................. 502/30 |
| 5,268,344 | 12/1993 | Pedrick et al. .............................. 502/30 |
| 5,283,216 | 2/1994 | Mitchell ...................................... 502/30 |
| 5,288,673 | 2/1994 | Behrmann et al. ......................... 502/30 |
| 5,382,748 | 1/1995 | Behrmann et al. ....................... 585/899 |

Primary Examiner—Gary Geist
Assistant Examiner—J. Parsa
Attorney, Agent, or Firm—Jay Simon

[57] ABSTRACT

A reversibly deactivated hydrocarbon synthesis catalyst in a hydrocarbon synthesis slurry is rejuvenated by successively passing the slurry through at least two rejuvenation stages external of the slurry reactor, each of which comprises a rejuvenation zone followed by an offgas removal zone. This is accomplished by using a lift pipe outside the reactor into which slurry from the reactor is passed and contacts a catalyst rejuvenating gas to partially rejuvenate the catalyst particles and form a rejuvenation offgas. The gas and slurry mixture are passed into a vessel in which the gas is removed from the slurry. Rejuvenation gas is bubbled into the slurry in the vessel to further rejuvenate the catalyst. A gas removing downcomer removes gas from the slurry in the vessel before it is passed back into the reactor. The rejuvenation gas also acts as a lift gas in the lift pipe.

17 Claims, 2 Drawing Sheets

SLURRY HYDROCARBON SYNTHESIS PROCESS WITH MULTISTAGE CATALYST REJUVENATION

BACKGROUND OF THE DISCLOSURE

FIELD OF THE INVENTION

The invention relates to a hydrocarbon synthesis process with multistage catalyst rejuvenation. More particularly, the invention relates to a process for rejuvenating solid catalyst particles in-situ in a three phase, Fischer-Tropsch type hydrocarbon synthesis slurry in a lift pipe and a combination gas separating and rejuvenation vessel external of the synthesis reactor, wherein the slurry comprises the catalyst particles, gas bubbles and a hydrocarbon slurry liquid.

BACKGROUND OF THE INVENTION

Slurry hydrocarbon synthesis (HCS) processes are known. In a slurry HCS process a synthesis gas (syngas) comprising a mixture of $H_2$ and CO is bubbled up as a third phase through a slurry in a reactor in which the slurry liquid comprises hydrocarbon products of the synthesis reaction and the dispersed, suspended solids comprise a suitable Fischer-Tropsch type hydrocarbon synthesis catalyst. Reactors which contain such a three phase slurry are sometimes referred to as "bubble columns", as is disclosed in U.S. Pat. No. 5,348,982. Irrespective of whether the slurry reactor is operated as a dispersed or slumped bed, the mixing conditions in the slurry will typically be somewhere between the two theoretical conditions of plug flow and back mixed. Syngas made from hydrocarbon feedstocks which contain nitrogen (i.e., natural gas) or nitrogen containing compounds (i.e., resids, coal, shale, coke, tar sands, etc.) invariably contains HCN and $NH_3$ which contaminate the reactive slurry and rapidly, but reversibly, deactivate the catalyst. Certain oxygenates and carbonaceous compounds which are formed in the slurry as by-products of the HCS reaction are also believed to cause rapid deactivation. Deactivation of such catalysts by these species is reversible and catalytic activity is restored (the catalyst rejuvenated) by contacting the deactivated catalyst with a hydrogen rejuvenating gas. The activity of the HCS catalyst in the reactive slurry may be intermittently or continuously rejuvenated by contacting the slurry with hydrogen or a hydrogen containing gas to form a catalyst rejuvenated slurry as is disclosed, for example, in U.S. Pat. Nos. 5,260,239 and 5,268,344. In the process of the '239 patent rejuvenation takes place in a vessel external to the slurry reactor in which the rejuvenating gas is bubbled up through the slurry.

It has been found that the catalyst rejuvenation process produces a rejuvenation offgas as a by-product, which contains species that are catalyst deactivating. In the prior art processes, the rejuvenating offgas mixes with the slurry in the reactor or in the external vessel. Permitting the offgas to contact and mix with the slurry recontaminates it with catalyst deactivating species, thereby limiting the overall efficiency of the catalyst rejuvenation process. Therefore, it would be an improvement in the art if the catalyst could be rejuvenated in the slurry without recontaminating it with catalyst deactivating species present in the rejuvenation offgas and in a manner which provides more contact time between the rejuvenating gas and the slurry.

SUMMARY OF THE INVENTION

The invention relates to a multistage process for rejuvenating reversibly deactivated solid catalyst particles in-situ in a three phase hydrocarbon synthesis (HCS) slurry external of the synthesis reaction zone, with reduced contamination or recontamination of the slurry with catalyst deactivating species in the offgas produced by the catalyst rejuvenation. By multistage is meant that the catalyst is rejuvenated in-situ in the slurry in at least two separate stages. The process of the invention comprises passing slurry from the HCS reactor through at least two rejuvenation zones external of the reactor, in each of which it contacts a rejuvenation gas which at least partially rejuvenates the catalyst in the slurry to form a mixture of a rejuvenated catalyst slurry and a gas product (offgas) of the rejuvenation. The offgas contains species which reversibly deactivate the catalyst and is removed from the slurry after each rejuvenation stage. After the last stage, the rejuvenated slurry is returned to the reactor. By stage is mean that the catalyst containing slurry is contacted with rejuvenating gas in a rejuvenating zone, followed by separating the offgas from the rejuvenated slurry before it is sent to the next stage or back into the reactor. In one embodiment, the first rejuvenation zone is an external, hollow lift pipe or conduit in internal fluid communication with the slurry in the reactor. Catalyst rejuvenating gas is injected into the lift pipe in which it mixes with the slurry and at least partially rejuvenates the catalyst particles. The rejuvenating gas also serves as a lift gas to lift the gas and slurry up through and out of the lift pipe and into the a gas disengaging and separating zone. The gas disengaging and separating zone is a separate vessel, also external of the HCS reactor. The disengaged and separated offgas is removed from the upper portion of the vessel and sent to further processing or disposal, while the rejuvenated catalyst slurry, reduced in offgas content, passes into the lower portion of the vessel. The vessel comprises a combination rejuvenation and gas removal zone. Rejuvenating gas is injected into the bottom of the vessel and bubbles up through the offgas-reduced slurry resulting from the first stage rejuvenation. This gas contacts the catalyst particles in the slurry for a second rejuvenation and produces a more fully rejuvenated catalyst slurry. One or more gas disengaging downcomers in the slurry in the vessel remove rejuvenating offgas and other gas bubbles from the slurry to form a gas reduced slurry, which is then passed back into the reactor through the downcomer. In yet a further embodiment, the slurry downcomer exiting the vessel may turn up and into another lift pipe into which rejuvenating gas is injected as a third rejuvenation zone, with the slurry and offgas produced by this third rejuvenation passed into the reactor through an appropriate gas separating means, so that the thrice rejuvenated slurry is passed into the reactor slurry after removal of the third stage offgas. Reactive slurry from the HCS reactor is passed into the lift pipe or first external rejuvenating zone by means of a gas disengaging downcomer, as is disclosed in the prior art, to remove at least a portion of the CO containing gas bubbles from the slurry before it enters the first rejuvenation zone. Unlike the prior art external rejuvenation process, the use of an external lift pipe enables the downcomer slurry entrance to be located further down in the reactive slurry where the catalyst concentration is typically greater, since slurry circulation through the lift pipe occurs as a result of the lifting action of the gas and not solely by gravity. The process of the invention provides more contact time between the catalyst containing slurry and rejuvenating gas. It is beneficial to remove as much unreacted CO containing synthesis gas as possible from the reactive slurry before it contacts the rejuvenating gas, as it has been found that the presence of CO in the slurry hinders catalyst rejuvenation until the CO has been consumed. In the context of the invention, the expressions "rejuvenated slurry" and "rejuvenated catalyst slurry" are used interchangeably and mean an HCS slurry in which the catalyst particles have been at least partially rejuvenated. By rejuvenated is meant the restoration of at least a portion of the catalytic activity for forming hydrocarbons from a synthesis gas (syngas) feed comprising a mixture of $H_2$ and CO.

In an embodiment with specific regard to a slurry HCS process, the process of the invention comprises the steps of:

(a) contacting a syngas comprising a mixture of $H_2$ and CO in the presence of catalyst deactivating species with a solid particulate hydrocarbon synthesis catalyst in a slurry body comprising said catalyst, hydrocarbon slurry liquid and gas bubbles, under reaction conditions effective to form hydrocarbons from said syngas, at least a portion of which are liquid at said reaction conditions, wherein said species present in said syngas reversibly deactivate said catalyst in said slurry;

(b) passing a portion of said slurry from said slurry body through a gas disengaging zone to remove CO containing gas bubbles from said slurry and form a CO reduced slurry;

(c) passing said gas reduced slurry into a first catalyst rejuvenation zone external of said slurry body;

(d) passing a gas comprising a catalyst rejuvenation gas into said first catalyst rejuvenation zone in which said gas contacts said slurry to at least partially rejuvenate said catalyst therein to form (i) a rejuvenated catalyst slurry and (ii) a rejuvenating offgas which contains species which will deactivate said catalyst and wherein said gas also acts as a lift gas in said zone;

(e) passing said rejuvenated catalyst slurry and offgas into a first gas separating and removal zone to disengage and separate said offgas from said slurry to form a first offgas lean rejuvenated catalyst slurry, and (f) repeating steps (c), (d) and (e) at least once by successively passing said first offgas lean rejuvenated slurry through at least one more combination of rejuvenation and offgas disengaging zones to form a final offgas lean rejuvenated catalyst slurry.

The final offgas lean rejuvenated catalyst slurry is then passed back into the slurry in the reactor or to any other desired location. In the practice of the invention, at least two rejuvenation-offgas separating stages are employed, although more may be used if desired. The deactivated catalyst present in the slurry may be concentrated in the slurry liquid before being passed into the first rejuvenation zone. The slurry reactor may be operating during rejuvenation or it may be taken off-line and batch rejuvenated. The rejuvenation may be conducted either continuously or on a cyclical basis. When rejuvenation occurs while the HCS reactor is on-line and producing hydrocarbon liquids, a portion of these liquids are either continuously or intermittently withdrawn from the reactor. These liquids are further processed into useful products.

The process of the invention avoids contaminating or recontaminating either or both the rejuvenated catalyst slurry and the slurry in the reactor with the deactivating offgas species formed by the catalyst rejuvenation, provides more complete catalyst rejuvenation in two or more stages, and more efficient offgas disengagement and removal than the prior art processes. It also enables better control of the rejuvenating temperature, because the rejuvenation zone is not immersed in the slurry or in the HCS reactor. In the context of the invention, the term "catalyst deactivating species" is meant to include species which reversibly deactivate the catalyst and wherein the catalyst activity is restored (the catalyst rejuvenated) by contact with a rejuvenating gas in-situ in the slurry liquid. Hydrogen or a hydrogen containing gas is useful for such rejuvenation, as has been demonstrated in the prior art. Finally, while HCN, $NH_3$ and certain types of oxygenates and carbonaceous materials will deactivate the catalyst, the invention is not intended to be limited to use only with these species, but is useful with any species which reversibly deactivate the catalyst and wherein the catalyst activity can be restored with an appropriate rejuvenating gas. Yet another advantage of the invention resides in the ability to achieve slurry circulation between the reactor, lift pipe, offgas disengaging and separating vessel and back into the reactor as a result of the lifting action of the rejuvenating gas in the lift pipe or pipes and by gravity. In this embodiment no slurry pumps are used or required. As set forth above, in one embodiment all of the stages are located external of the slurry reactor. In another embodiment, one or more stages may be located in the reactor, with at least two stages located external of the reactor. Finally, it will be appreciated that while the practice of the invention finds particular use with rejuvenating an HCS catalyst in-situ in a hydrocarbon slurry liquid, it is not intended to be limited to this particular embodiment.

DETAILED DESCRIPTION

Figure 1:
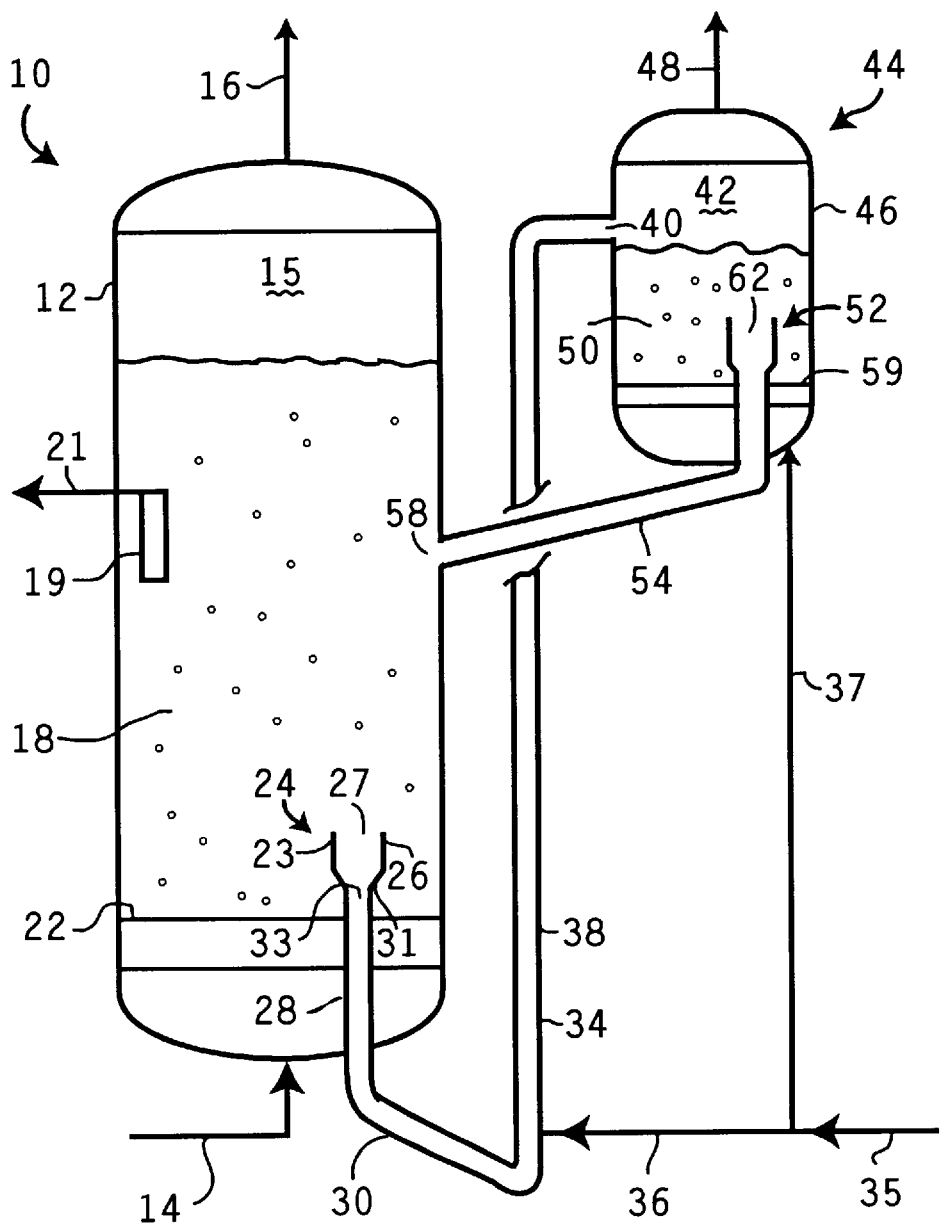
FIG. 1 is a schematic cross section of an HCS slurry reactor according to the process of the invention with first second stage catalyst rejuvenation external of the slurry reactor.

In a Fischer-Tropsch slurry HCS process, a syngas comprising a mixture of $H_2$ and CO is bubbled up into a reactive slurry in which it is catalytically converted into hydrocarbons and preferably liquid hydrocarbons. The mole ratio of the hydrogen to the carbon monoxide may broadly range from about 0.5 to 4, but which is more typically within the range of from about 0.7 to 2.75 and preferably from about 0.7 to 2.5. The stoichiometric mole ratio for a Fischer-Tropsch HCS reaction is 2.0, but there are many reasons for using other than a stoichiometric ratio as those skilled in the art know and a discussion of which is beyond the scope of the present invention. In a slurry HCS process the mole ratio of the $H_2$ to CO is typically about 2.1/1. The syngas may be formed by various means, including contacting a hot carbonaceous material such as coke or coal, with steam, or from a feed comprising methane. A feed comprising methane is preferred for convenience, cleanliness and because it doesn't leave large quantities of ash to be handled and disposed of The methane containing gas feed is fed into a syngas generator and is obtained from natural gas or by burning coal, tar, liquid hydrocarbons and the like. The production of syngas from methane by either partial oxidation, steam reforming or a combination thereof is well known as is disclosed, for example, in U.S. Pat. No. 4,888,131. In many cases it is preferred to catalytically partially oxidize and steam reform the methane in a fluid bed syngas generating unit (FBSG) as is disclosed, for example, in U.S. Pat. Nos. 4,888,131 and 5,160,456. Irrespective of the source of the methane, nitrogen or nitrogen containing compounds are typically present in the methane containing gas fed into the syngas generator, some of which are converted into $NH_3$ and HCN during the syngas formation. These will deactivate a Fischer-Tropsch HCS catalyst, particularly those comprising Co as the catalytic metal, and it is difficult and expensive to remove them to the extent that they are not present in amounts that will not result in catalyst deactivation over reasonable periods of time. It has been found that deactivation by these species is reversible and the catalyst can be rejuvenated by contacting it with hydrogen. This restoration of the catalytic activity of a reversibly deactivated catalyst is referred to as catalyst rejuvenation. However, while preferred and possible, complete restoration of the catalytic activity for all of the catalyst particles in the slurry passing through the rejuvenation tube may not always be achieved in the process of the invention. It's for this reason the expression "at least partially rejuvenates the catalyst" and the like, are used herein. It has been found that the rejuvenation process produces a rejuvenation product gas, which has been referred to herein as a rejuvenation offgas, and that this offgas contains some of the same catalyst deactivating species present in the syngas which resulted in the catalyst deactivation in the first place (e.g., $NH_3$ and HCN). Therefore it is important to remove the offgas from the rejuvenated slurry before it is passed back into the main slurry body in the HCS reactor to avoid recontaminating the reactive slurry with the catalyst deactivating species. The net effect can be that very little benefit is gained by the rejuvenation process and, consequently, a way had to be found to remove the offgas from the rejuvenated slurry in a manner which did not result in recontamination of the reactive HCS slurry with the catalyst deactivating species. The present invention is a solution to this problem.

The presence of CO in the rejuvenation zone hinders catalyst rejuvenation until the CO is consumed. Thus, removing at least a portion of the gas bubbles which contain unreacted syngas from the slurry before it is passed into the rejuvenation zone, substantially reduces the amount of CO present in the rejuvenation zone. This reduces the amount of hydrogen needed for the rejuvenation and results in a greater degree of rejuvenation. Further, due to the injection of the hydrogen or hydrogen containing rejuvenation-lift gas into the rejuvenation zone, the $H_2$ to CO ratio in the rejuvenation zone is substantially greater than the stoichiometric 2.1/1 and may be higher than 10/1. This means that instead of being converted to more desirable liquid hydrocarbon products, the CO in the rejuvenation zone is converted primarily to methane, thereby wasting valuable syngas and some of the added hydrogen rejuvenating gas. These gas bubbles also contain gas reaction products of the HCS reaction, of which 50% or more may be water vapor, which interferes with the catalyst rejuvenation by acting as a diluent for the rejuvenation gas. Reacting CO with $H_2$ is exothermic. Reacting out the CO with $H_2$ in the rejuvenation zone, instead of at least partially removing the gas bubbles from the slurry before it passes into the rejuvenation and contacts the hydrogen or hydrogen containing rejuvenation gas, increases the slurry temperature. This also favors methane production from the CO and tends to promote hydrogenolysis and cracking of the hydrocarbon liquid to lighter products, such as methane. For these reasons it is beneficial to remove as much of the gas bubbles as is possible from the slurry before it is rejuvenated.

One embodiment of the invention is illustrated in schematic cross section in FIG. 1 in which a slurry type HCS reactor 10, comprising a cylindrical steel vessel 12 containing a three phase slurry 18 within, a gas line 14 for feeding the syngas feed into the bottom of the reactor, and a gas product line 16 at the top for removing gas products of the Fischer-Tropsch type HCS reaction and unreacted syngas which rise up out of the slurry and collect in gas space 15. The slurry comprises hydrocarbon liquid in which is dispersed and suspended a particulate HCS catalyst and gas bubbles. The slurry liquid comprises HCS reaction products which are liquid at the slurry reaction conditions and the gas bubbles comprise the uprising syngas, along with gas products of the HCS reaction, a significant amount of which comprises steam or water vapor. The syngas is bubbled up into the bottom of slurry 18 through suitable gas distribution means located across the surface of an otherwise gas and liquid impermeable tray 22, located near the bottom of the reactor. A hydrocarbon liquid product withdrawal means 19, such as a filter, is located within the main slurry body 18 for withdrawing liquid hydrocarbon products from the reactor, via line 21. A gas disengaging downcomer 24 includes a substantially vertical, hollow conduit 28 which opens at its top into a vertically extending and upward opening gas disengaging means 26, for disengaging gas bubbles from the slurry. Means 26 also concentrates catalyst particles in the slurry liquid flowing down and out opening 33 into vertical, hollow downcomer conduit 28. Conduit 28 exits the reactor and extends laterally over as an angled transverse portion 30, which turns upward at its bottom 32 into lift pipe 34 and is in fluid communication with the interior catalyst rejuvenating zone 38 of the lift pipe. The gas disengaging and catalyst concentrating means 26 comprises a hollow cup having a cylindrical, vertical outer wall 23 and a sloping bottom 31 which define an interior gas disengaging and catalyst concentrating zone, indicated as 27. The angle of the sloping bottom 31 and also that of the transverse portion 30 of the downcomer 28 is greater than the angle of internal friction of the catalyst particles, so that catalyst particles disengaged from the slurry don't build up on the bottom. In this embodiment, means 26 is an upwardly opening cup, having a hollow cylindrical, outer wall 23, which extends upwardly and which, together with bottom 31, defines the space 27 within. However, it could have a rectilinear, curvilinear or polygonal outer wall. In the embodiment illustrated in FIG. 1, the gas disengaging cup 26 resembles a funnel having a vertically upward extending outer wall, or a bucket with a sloping bottom. Other geometries may be used at the convenience and discretion of the practitioner. The essential features of means or cup 26 include the upwardly opening gas disengaging and (optionally) catalyst concentrating zone 27, surrounded by peripheral wall 23, sloping bottom 31 and bottom orifice or slurry exit 33. The cup must be open at the top to permit slurry to enter and, at the same time, permit disengaged gas to exit. Wall 23 and bottom 31 prevent the upwardly rising gas bubbles, indicated by small circles, from entering up into the slurry in the cup or, to permit gas disengagement and, if desired, concentrate the catalyst. It is also sized so as to provide enough residence time for the slurry flowing therethrough to achieve a more quiescent, preferably laminar downward flow, to permit maximum coalescence and release of the gas bubbles in the slurry, before it flows down into the vertical downcomer 28. This permits the suspended catalyst particles to drop out and concentrate in the slurry liquid entering the downcomer through opening 33, which is smaller than the opening at the top of the cup which is both the slurry entrance and the disengaged gas exit. That is, the horizontal cross section of the gas disengaging cup is significantly larger than that of the orifice in the bottom of the cup, to achieve a greater net concentration of catalyst in the downcomer than in the main slurry body 18. The increased catalyst concentration is due in part to the release of the gas bubbles which results in a denser slurry having a net greater catalyst content than in the main slurry body 18. Further, while there is considerable turbulence in the slurry bed 18, slurry just above zone 27, but not in the cup, will also drop catalyst, due to a decreased amount of uprising gas bubbles present immediately above the zone which serve to keep the catalyst particles in suspension. As shown in the Figure, the bottom of downcomer 28 exits the slurry and the reactor and bends laterally over as transverse portion 30 which turns upward at its bottom 32 into hollow lift pipe 34, the interior 38 of which is the catalyst rejuvenating zone. Thus, reactive slurry from the slurry body 18 in the reactor 10 flows down into the gas disengaging and catalyst concentrating zone 27, of the downcomer 24 in which the slurry disengages gas bubbles to form a gas reduced slurry and, at the same time concentrates the catalyst so that the slurry flowing down and out of the cup or zone 27, via orifice 31 and into downcomer conduits 28 and 30, is both gas reduced and catalyst concentrated, compared to the slurry in the main slurry body 18 from which the slurry is withdrawn. Although concentrating the catalyst in the gas reduced slurry fed into the lift pipe may be optional in some embodiments, it is a preferred embodiment in the practice of the invention when used with a three phase HCS slurry. The gas reduced and catalyst concentrated slurry then passes down the downcomer conduit, out of the reactor, over and up into the interior, first stage catalyst rejuvenating zone 38, of lift pipe 34. Rejuvenating gas comprising hydrogen is passed, via lines 35 and 36, into the interior 38 of lift pipe 34 near the bottom thereof, in which it contacts the catalyst in the gas reduced slurry liquid to at least partially rejuvenate it and form a first stage rejuvenated catalyst slurry and rejuvenating offgas. The rejuvenating gas also acts as a lift gas to lift the slurry containing the rejuvenated catalyst up, over and out of the upper opening 40 and into gas disengaging and separating zone 42 in vessel 44. Vessel 44 comprises an outer cylindrical wall 46, an upper gas separating and removal zone 42 from which offgas and unreacted rejuvenating gas are removed via gas line 48. Vessel 44 also contains slurry 50 within, which comprises a mixture of the offgas reduced first stage rejuvenated catalyst slurry and a second stage rejuvenated catalyst slurry. At least one gas disengaging downcomer 52, identical in most respects to downcomer 26 in having an upper gas disengaging cup from which a vertical downcomer conduit depends, extending over as transverse portion 54, feeds offgas disengaged and reduced second stage rejuvenated slurry back into the slurry reactor 10. In the embodiment shown, only one downcomer 52 is illustrated for the sake of convenience. However, a plurality of such downcomers may be employed, which feed into one or more manifolds or larger conduits and the like, for returning the second and (in this embodiment) final stage rejuvenated slurry back into the main slurry body in the reactor as shown, or to further processing. Catalyst rejuvenating gas is injected up into the bottom of slurry 50 via gas lines 35 and 37 and through suitable gas distribution means arrayed across an otherwise gas and liquid impermeable tray 59, as in reactor 10. The mixture of offgas and first stage rejuvenated slurry exits first stage rejuvenation zone 38 and into gas separating and removal zone 42 via orifice or opening 40 in which the offgas separates from the rejuvenated slurry and is removed via overhead gas line 48. The offgas reduced, first stage rejuvenated slurry passes down into slurry 50 in vessel 44 and is again contacted with the uprising rejuvenating gas bubbling up through it which further and more fully rejuvenates the catalyst in the slurry to form a second stage rejuvenated slurry and offgas. The offgas rises up through the slurry into gas separating zone 42 and is removed from the vessel. Bubbles of offgas remaining in the second stage rejuvenated slurry are disengaged from the slurry as it passes into the gas disengaging zone 62 in cup 64. The disengaged gas passes up and is assisted in its upward rise by the unreacted and uprising bubbles of rejuvenating gas. Thus, the second stage rejuvenated slurry containing more fully rejuvenated catalyst particles and substantially free of offgas is passed down through the downcomer 54 and back into the slurry body 18 in HCS reactor 10. The offgas removed from the vessel is rich in hydrogen and is consumed as fuel or, more preferably, sent to further processing to clean up the gas by removing the catalyst deactivating species and form a clean gas of which all, or a portion, may be used in other processing or recycled back into the lift pipe and vessel as catalyst rejuvenating gas. While the outboard or external slurry catalyst rejuvenation means used to describe the process of the invention is shown as a lift pipe in the form of a cylindrical, hollow conduit or pipe, there are other embodiments in which the lift pipe may be vertically baffled into a plurality of vertically rising catalyst rejuvenation zones, have a rectilinear or polygonal, etc. cross section and be fed slurry containing at least partially deactivated catalyst via a manifold into which a number of downcomers present in a slurry body feed a gas depleted and, optionally, catalyst concentrated slurry. In such an embodiment the rejuvenating gas will be injected up into each rejuvenation zone.

In another embodiment of the practice of the invention which is not shown, but which will be understood and appreciated by those skilled in the art, the downcomer (or more than one such downcomers) 54 may extend down and then turn up into a second lift pipe or vertical rejuvenating conduit into which rejuvenating gas is injected to form a third rejuvenation zone. This top of this second lift pipe will exit into a second outboard vessel similar to 44, in which the offgas is removed and separated from the more fully rejuvenated slurry. This three times rejuvenated slurry is fed into a gas disengaging downcomer in the vessel and fed back into the reactor, as is disclosed in the embodiment above. Alternatively, the second lift pipe rejuvenation zone may feed the three times rejuvenated slurry back into the reactor into a gas separating and disengaging zone to separate and remove the offgas before the three times rejuvenated slurry is passed back into the reactive slurry in reactor 10.

Figure 2:
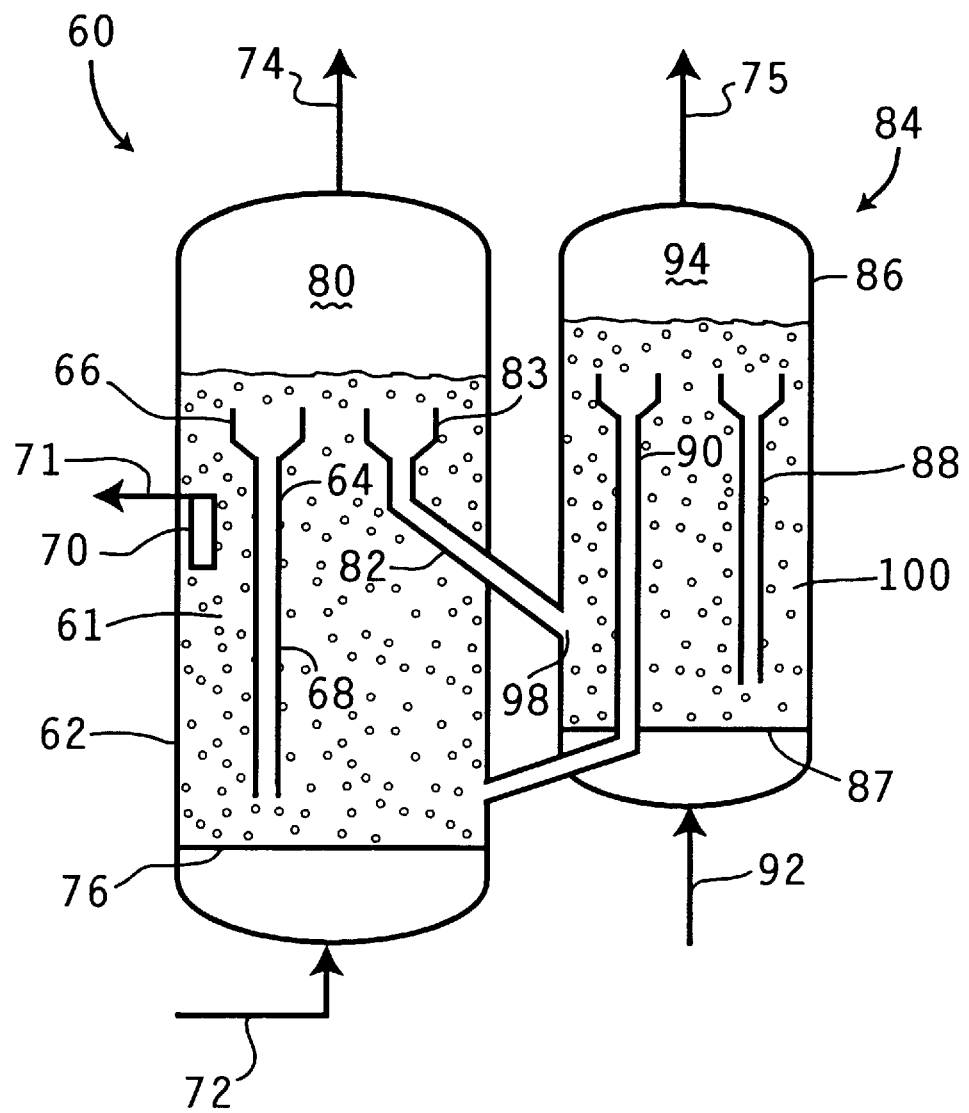
FIG. 2 schematically represents a HCS slurry catalyst rejuvenation process of the prior art in which catalyst is rejuvenated in a single stage external of the slurry reactor.

FIG. 2 represents an outboard slurry rejuvenation process of the prior art as disclosed in U.S. Pat. No. 5,260,239, in which an HCS slurry reactor 60 comprising a cylindrical shell 62 contains a three phase slurry 61 within which comprises catalyst particles and gas bubbles dispersed and suspended in a slurry liquid. One or more gas disengaging downcomers for reducing catalyst maldistribution, of which only one (64) is shown for the sake of convenience, comprise an upper gas disengaging and catalyst concentrating cup from which depends a vertical downcomer pipe 68. This gas disengaging downcomer is of the type disclosed and claimed in U.S. Pat. No. 5,382,748. Slurry liquid removal means 70, such as a filter, removes liquid products of the HCS reaction from the reactor via line 71. Feed gas line 72 feeds a syngas into the bottom of the reactor which is distributed up into the slurry via a plurality of gas distributing means arrayed across an otherwise gas and liquid impermeable tray 76. The top of the reactor comprises a gas collecting zone 80 from which gas is removed from the reactor via line 74. Another downcomer, 82, is shown also comprising a gas disengaging and catalyst concentrating cup 83 at the top of a hollow conduit which depends generally vertically downward from the cup, bends down and over out of the reactor and into catalyst rejuvenation vessel 84, into which it feeds a gas depleted and catalyst concentrated slurry from the slurry body 61 in the reactor. Catalyst rejuvenation vessel 84 comprises a cylindrical outer shell 86, one or more catalyst distributing downcomers, of only one is shown (88) for the sake of convenience, for maintaining a more even, vertical catalyst concentration in the vessel. It also contains a one or more downcomers, of which only one (90) is shown for the sake of convenience, which returns rejuvenated slurry back into reactor 60. Vessel 84 has an interior gas collecting zone 94 proximate the top of the vessel and gas is removed therefrom via gas line 75. One or more gas disengaging and catalyst concentrating downcomers 82 in HCS reactor 60 feed gas reduced and catalyst concentrated slurry, in which the catalyst is at least partially reversibly deactivated, from the reactor into catalyst rejuvenation vessel 84 via one or more orifices 98. In vessel 84 the gas reduced and catalyst concentrated slurry is contacted with a catalyst rejuvenating gas comprising hydrogen introduced into the bottom of the vessel via line 92, and bubbles up through the slurry 100 in the vessel, through suitable gas distribution means in an otherwise gas and liquid impermeable tray 87. The rejuvenating gas at least partially restores the activity of the catalyst particles in the slurry, a portion of which continuously passes into the gas disengaging zones of the one or more downcomers 90 which return the slurry back into the reactor. Rejuvenating offgas removed from the catalyst rejuvenated slurry contacts the slurry in the rejuvenation vessel. The hydrogen or hydrogen containing catalyst rejuvenation gas injected into the rejuvenation zone comprises hydrogen which may contain other gasses such as nitrogen, $CO_2$, $H_2O$, $CH_4$, $C_2$–$C_{4+}$ hydrocarbons, and also CO (as long as the mole ratio of the $H_2$ to CO) is sufficient to remove the CO and still rejuvenate at least a portion of the catalyst. In one embodiment referred to above, all or a portion of the hydrogen containing rejuvenating offgas may be recycled back into the rejuvenation zones, after it has been treated to remove catalyst poisons such as oxygenates and nitrogen compounds referred to above. This can be done physically in one or more solid adsorbent beds, by cooling and dissolving in water, etc.

As disclosed in U.S. Pat. No. 5,288,673, the degree of catalyst rejuvenation can be controlled by independently controlling the slurry temperature in the rejuvenating zone irrespective of the temperature of the main body of slurry in the surrounding HCS reaction zone. This patent discloses that temperature control in the rejuvenation zone or tubes is achieved by one or more of either increasing or decreasing the slurry residence time in the zone, so as to utilize the exothermic nature of the rejuvenation reactions, by insulating the rejuvenation tubes, by introducing heat or a cooling medium into the zone, by preheating the rejuvenating gas, etc. The '673 patent teaches that the temperature in the rejuvenation zone should be high enough to remove CO and at least partially rejuvenate the catalyst and low enough to minimize methane formation and wax (~$C_{20+}$ alkanes) hydrolysis. These teachings apply to the present invention also.

In an HCS process, liquid and gaseous hydrocarbon products are formed by contacting a syngas comprising a mixture of $H_2$ and CO with a Fischer-Tropsch type of HCS catalyst, under shifting or non-shifting conditions and preferably under non-shifting conditions in which little or no water gas shift reaction occurs, particularly when the catalytic metal comprises Co, Ru or mixture thereof Suitable Fischer-Tropsch reaction types of catalyst comprise, for example, one or more Group VIII catalytic metals such as Fe, Ni, Co, Ru and Re. In one embodiment the catalyst comprises catalytically effective amounts of Co and one or more of Re, Ru, Fe, Ni, Th, Zr, Hf, U, Mg and La on a suitable inorganic support material, preferably one which comprises one or more refractory metal oxides. Preferred supports for Co containing catalysts comprise titania, particularly when employing a slurry HCS process in which higher molecular weight, primarily paraffinic liquid hydrocarbon products are desired. Useful catalysts and their preparation are known and illustrative, but nonlimiting examples may be found, for example, in U.S. Pat. Nos. 4,568,663; 4,663,305; 4,542,122; 4,621,072 and 5,545,674.

The hydrocarbons produced by an HCS process according to the invention are typically upgraded to more valuable products, by subjecting all or a portion of the $C_{5+}$ hydrocarbons to fractionation and/or conversion. By conversion is meant one or more operations in which the molecular structure of at least a portion of the hydrocarbon is changed and includes both noncatalytic processing (e.g., steam cracking), and catalytic processing (e.g., catalytic cracking) in which a fraction is contacted with a suitable catalyst. If hydrogen is present as a reactant, such process steps are typically referred to as hydroconversion and include, for example, hydroisomerization, hydrocracking, hydrodewaxing, hydrorefining and the more severe hydrorefining referred to as hydrotreating, all conducted at conditions well known in the literature for hydroconversion of hydrocarbon feeds, including hydrocarbon feeds rich in paraffins. Illustrative, but nonlimiting examples of more valuable products formed by conversion include one or more of a synthetic crude oil, liquid fuel, olefins, solvents, lubricating, industrial or medicinal oil, waxy hydrocarbons, nitrogen and oxygen containing compounds, and the like. Liquid fuel includes one or more of motor gasoline, diesel fuel, jet fuel, and kerosene, while lubricating oil includes, for example, automotive, jet, turbine and metal working oils. Industrial oil includes well drilling fluids, agricultural oils, heat transfer fluids and the like.

It is understood that various other embodiments and modifications in the practice of the invention will be apparent to, and can be readily made by, those skilled in the art without departing from the scope and spirit of the invention described above. Accordingly, it is not intended that the scope of the claims appended hereto be limited to the exact description set forth above, but rather that the claims be construed as encompassing all of the features of patentable novelty which reside in the present invention, including all the features and embodiments which would be treated as equivalents thereof by those skilled in the art to which the invention pertains.

What is claimed is:

1. A process for rejuvenating a reversibly deactivated particulate hydrocarbon synthesis catalyst in a slurry comprising said catalyst particles and gas bubbles in a hydrocarbon slurry liquid which comprises products of a slurry hydrocarbon synthesis process which are liquid at the hydrocarbon synthesis reaction conditions, said process comprising withdrawing a portion of said slurry from a slurry reactor and successively passing it through at least two catalyst rejuvenation stages external of said reactor, wherein each said stage sequentially comprises (i) a rejuvenation zone in which said slurry contacts a catalyst rejuvenating gas form a slurry in which said particles are at least partially rejuvenated to form a rejuvenated catalyst slurry and a rejuvenation offgas and (ii) an offgas separating zone in which said offgas is separated and removed from said rejuvenated slurry, and wherein the first stage rejuvenation zone comprises a lift pipe or hollow conduit into which said rejuvenating gas is injected to at least partially rejuvenate said slurry and lift it through and out of said conduit and into a first stage offgas separating and removal zone.

2. A process according to claim 1 in which slurry circulation between said reactor and rejuvenation stages occurs by means of said rejuvenation gas and gravity.

3. A process according to claim 1 wherein said second stage comprises a vessel containing at least partially rejuvenated slurry, above which is a space which comprises an offgas separating and removal zone for said first and second stages.

4. A process according to claim 3 wherein said catalyst comprises one or more supported Group VIII metals which includes cobalt.

5. A slurry hydrocarbon synthesis process for forming hydrocarbons which comprises:
  (a) contacting a synthesis gas comprising a mixture of $H_2$ and CO in the presence of catalyst deactivating species with a solid particulate hydrocarbon synthesis catalyst in a slurry body comprising said catalyst and gas bubbles in a hydrocarbon slurry liquid, under reaction conditions effective to form hydrocarbons from said synthesis gas, at least a portion of which are liquid at said reaction conditions, wherein said species present in said synthesis gas reversibly deactivate said catalyst in said slurry;
  (b) passing slurry from said slurry body into a first catalyst rejuvenation zone comprising a lift pipe or hollow conduit external of said body;
  (c) passing a gas comprising a catalyst rejuvenation gas into said first catalyst rejuvenation zone in which said gas contacts said slurry to at least partially rejuvenate said catalyst therein to form a mixture of (i) a rejuvenated catalyst slurry and (ii) a rejuvenating offgas which contains species which will deactivate said catalyst and wherein said rejuvenation gas also acts as a lift gas in said zone;
  (d) passing said mixture through and out of said conduit and into a first gas separating and removal zone by means of said lift gas to separate and remove said offgas from said slurry to form a first offgas reduced rejuvenated catalyst slurry, and
  (e) passing said first offgas reduced, rejuvenated slurry through at least one more combination of rejuvenation and offgas separation and removal zones to form a final offgas reduced and more fully rejuvenated catalyst slurry.

6. A process according to claim 5 wherein said slurry in said slurry body contains gas bubbles, wherein a portion of said gas in said bubbles is CO and wherein at least a portion of said bubbles are removed from said slurry before it is passed into said first rejuvenation zone.

7. A process according to claim 6 wherein said catalyst comprises at least one supported Group VIII metal.

8. A process according to claim 7 wherein the last offgas reduced, rejuvenated catalyst slurry is passed back into said slurry body.

9. A process according to claim 8 wherein at least a portion of said hydrocarbons formed from said synthesis gas are upgraded by one or more conversion operations to at least one product.

10. A process according to claim 9 wherein said metal comprises cobalt.

11. A process according to claim 1 wherein said conduit is in fluid communication with said slurry in said reactor.

12. A process according to claim 11 wherein said offgas reduced slurry from said last rejuvenation stage is passed back into said reactor.

13. A process according to claim 12 wherein said offgas contains unreacted hydrogen and catalyst deactivating species and is recycled back as part of said rejuvenating gas after being processed to remove said species from said gas.

14. A process according to claim 8 wherein said first rejuvenation zone is in fluid communication with said slurry body.

15. A process according to claim 14 wherein said offgas contains unreacted hydrogen and catalyst deactivating species and is recycled back as part of said rejuvenating gas after being processed to remove said species from said gas.

16. A process according to claim 1 wherein all or a portion of $C_{5+}$ hydrocarbons produced by said hydrocarbon synthesis process are upgraded to more valuable products by fractionation and/or a conversion operation in which the molecular structure of at least a portion of said hydrocarbons is changed.

17. A process according to claim 15 wherein all or a portion of $C_{5+}$ hydrocarbons produced by said hydrocarbon synthesis process are upgraded to more valuable products by fractionation and/or a conversion operation in which the molecular structure of at least a portion of said hydrocarbons is changed.

* * * * *